(12) United States Patent
Bailey

(10) Patent No.: US 11,224,448 B2
(45) Date of Patent: Jan. 18, 2022

(54) METHOD AND SYSTEM FOR MINIMALLY INVASIVE BONE EXTRA-ARTICULAR RECONSTRUCTION

(71) Applicant: Erroll J. Bailey, Atlanta, GA (US)

(72) Inventor: Erroll J. Bailey, Atlanta, GA (US)

( * ) Notice: Subject to any disclaimer, the term of this patent is extended or adjusted under 35 U.S.C. 154(b) by 43 days.

(21) Appl. No.: 16/913,447

(22) Filed: Jun. 26, 2020

(65) Prior Publication Data
US 2020/0405328 A1 Dec. 31, 2020

Related U.S. Application Data

(60) Provisional application No. 62/867,850, filed on Jun. 27, 2019.

(51) Int. Cl.
| | | |
|---|---|---|
| A61B 17/17 | (2006.01) | |
| A61B 17/16 | (2006.01) | |
| A61B 17/00 | (2006.01) | |
| A61B 17/15 | (2006.01) | |

(52) U.S. Cl.
CPC .... *A61B 17/1775* (2016.11); *A61B 17/00234* (2013.01); *A61B 17/151* (2013.01); *A61B 17/1682* (2013.01); *A61B 17/1697* (2013.01); *A61B 17/1728* (2013.01); *A61B 17/1796* (2013.01)

(58) Field of Classification Search
CPC .............. A61B 17/1775; A61B 17/151; A61B 17/1682
See application file for complete search history.

(56) References Cited

U.S. PATENT DOCUMENTS

| | | | | |
|---|---|---|---|---|
| 5,843,085 A * | 12/1998 | Graser | ................. | A61B 17/151 606/87 |
| 7,972,338 B2 * | 7/2011 | O'Brien | ............... | A61B 17/152 606/87 |
| 8,388,690 B2 * | 3/2013 | Singhatat | ........... | A61B 17/1728 623/23.51 |
| 9,317,631 B2 * | 4/2016 | Davison | ................. | A61B 34/20 |
| 10,039,559 B2 * | 8/2018 | Awtrey | ................ | A61B 17/152 |
| 2002/0055744 A1 * | 5/2002 | Reiley | .................... | A61B 17/15 606/79 |

(Continued)

OTHER PUBLICATIONS

Acquired adult flat foot secondary to posterior tibial-tendon pathology; DA Funk, JR Cass, KA Johnson; Abstract Only.

(Continued)

*Primary Examiner* — Christian A Sevilla
(74) *Attorney, Agent, or Firm* — Jeffrey F. Yee; Lewis, Brisbois, Bisgaard & Smith LLP

(57) ABSTRACT

A method and system for performing corrective surgery for pediatric or adult acquired flatfoot deformity ("AAFD"), namely, minimally invasive bone extra-articular reconstruction. The method and system comprises attaching a cutting guide to the bone to be operated wherein the cutting guide comprises two or more diverging K-wire channels and a slit configured to guide a burr used by a surgeon to perform osteotomy through the slit. Through the use of the cutting guide, the surgical procedure is simpler and reproducible. Patients will experience a quicker recovery, less pain, less operating room time, less narcotic use, and a better cosmetic result from smaller incisions. The present invention may also be applicable to intra-articular applications.

10 Claims, 6 Drawing Sheets

(56) References Cited

U.S. PATENT DOCUMENTS

2018/0110530 A1* 4/2018 Wagner ............... A61B 17/151

OTHER PUBLICATIONS

Rupture of the posterior tibial tendon causing flat foot. Surgical treatment.; Mann, R.A.; Thompson, JBJS; Apr. 1985—vol. 67—Issue 4 p. 556-561; Abstract Only.
Treatment of Stage II posterior tibial tendon deficiency with flexor digitorum longus tendon transfer and calcaneal osteotomy; M. Myerson et al.; Abstract Only.
Acquired Flatfoot in Adults Due to Dysfunction of Posterior Tibial Tendon; G. Pomeroy; et al; vol. S1-A, No. 8, Aug. 1999; pp. 1173-1182.
Posterior Tibial Tendon Insufficiency: Diagnosis and Treatment: T. Beals, et al.; Journal of the American Academy of Orthopaedic Surgeons: Mar. 1999 vol. 7 Issue 2, pp. 112-118, Abstract only.
The Effects of a Medializing Calcaneal Osteotomy with and without Superior Translation on Achilles Tendon Elongation and Plantar Foot Pressures; M. Hadfield, M.D., et al.; May 1, 2005 Research Article.
Calcaneal Osteotomy and Transfer of the tendon of flexor digitorum longus for stage-II dysfunction of tibialis posterior. Three-to-five year results; J. Wacker, et al.; Abstract Only.
Flexor digitorum longus transfer ad medial displacement calcaneal osteotomy for posterior tibial tendon dysfunction: a middle-term clinical follow-up; G. Guyton, et al.; Abstract Only.
Treatment of stage II posterior tibial tendon dysfunction with flexor hallucis longus transfer and medial displacement calcaneal osteotomy; G. Sammarco; Abstract Only.
The Effects of a Medializing Calcaneal Osteotomy with and without Superior Translation on Achilles Tendon Elongation and Plantar Foot Pressures; M. Hadfield, M.D., et al.; First Published May 1, 2005; Research Article.
Plantar Measurements to Determine Success of Surgical Correction of Stage IIb Adult Acquired Flatfoot Deformity; E. Matheis MS, et al.; Abstract Only.
A biomechanical model of the foot; EP Salathe Jr.; Abstract Only.
Biomechanical study of stress in the fifth metatarsal; G.A. Arangio; Abstract Only.
Flexor digitorum longus transfer with medial displacement calcaneal osteotomy. Biomechanical rational; D. Hartog; Foot and Ankle Clinics, Feb. 28, 2001; Abstract Only.
Medial Displacement Calcaneal Osteotomy: A Comparison of Screw Versus Locking Plate Fixation; J. Foot ANkle Sung; Nov. 2016-Dec.; 55: 1164-1168; Abstract.
Minimally invasive calcaneal osteotomy; a safe alternative to open calcaneal osteotomy with fewer complications; A. Kendal, et al. Published Feb. 21, 2018.
Minimally invasive calcaneal osteotomy: A cadaveric and clinical evaluation; C. Jowelt, et al. https://dai.org/10.1016/j.fas.2015.11.001.
Medial Displacement Calcaneal Osteotomy Using Minimally Invasive Technique; E. Kheir et al.
Congenital club foot in children younger than 24 months: Decancelous Cuboid Combined with Selective Soft Tissue Release; Nguyen Ngoc Hung; Article Citations.
Calcaneal Lengthening For Valgus deformity of the hindfoot. Results in children who had severe, symptomatic flatfoot and skewfoot; V.S. Mosca; Abstract Only.
Effect of calcaneal lengthening on relationships among the hindfoot, midfoot, and forefoot; B.J. Sangeorzan, et al, Abstract Only.
Calcaneal Lengthening: Investigation of deformity correction in a cadaver flatfoot model; T. Dumontier, et al; Abstract Only.
Lateral Column Lengthening for Acquired Adult Flatfoot Deformity Caused by Posterior Tibial Tendon Dysfunction Stage II: A Retrospective: Abstract Only.
Modified Evans Osteotomy for the operative treatment of acquired pes planovalgus; H. Zwipp, et al; Abstract Only.
Lengthening of the Lateral Column and Reconstruction of the Medial Soft Tissue for Treatment of Acquired Flatfoot Deformity Associated with Insufficiency of the Posterior Tibial Tendon; B. Hintermann, M.D., et al. Abstract Only.
Calcaneocuboid Joint Pressure After Lateral Column Lengthening in a Cadaveric Planovalgus Deformity Model, N. Momberger M.D., et al; First Published Sep. 1, 2000.
Evans Osteotomy Complications; M. Jara; Abstract Only.
Calcaneal Osteotomies; F. Malerba, et al.; Abstract Only.
Double Calcaneal osteotomy in the treatment of posterior tibial tendon dysfunction; J. Frankel, et al; Abstract.
Calcaneal Osteotomies for the treatment of Adult-Acquired Flatfoot; https://doi.org/10.1016/j.com.2007.07.002.
Calcaneal osteotomy in the treatment of adult acquired flatfoot deformity; Guha AR, et al; Abstract Only.
Biomechanical Assessment of Flexible Flatfoot Correction; Comparislon of Techniques in a Cadaver Model; Zanolli, D. et al; The Journal of Bone & Joint Surgery: Mar. 19, 2014 vol. 96 Issue 6; Abstract Only.
A biomechanical model of the foot; E.P. Salathe Jr., et al; Abstract Only.
A biomechanical analysis of posterior tibial tendon dysfunction, medial displacement calcaneal osteotomy and flexor digitorum longus transfer in adult acquired flat foot; G. Arangio, et al.; Abstract Only.
Minimally Invasive Osteotomies, D. Redfern, et al; Abstract Only.
Plantarflexion Opening Wedge Medial Cuneiform Osteotomy for Correction of Fixed Forefoot Varus Associated with Flatfoot Deformity; C. Hirose MD, et al; Abstract Only.
Postoperative Medial Cuneiform Position Correlation with Patient-Reported Outcomes following cotton osteotomy for reconstruction of the stage II Adult-Acquired Flatfoot Deformity; M. Conti, M.D., et al; Abstract Only.
Radiographic Analysis of an Opening Wedge Osteotomy of the Medial Cuneiform, M. Lutz Fracs, et al., First Published Mar. 1, 2011; Abstract Only.
Contribution of Medial Cuneiform Osteotomy to Correction of Longitudinal Arch Collapse in Stage IIb Adult-Acquired Flatfoot Deformity; K. GC, et al; Foot & Ankle International, Apr. 4, 2018; Abstract Only.
Postoperative Medial Cuneiform Position Correlation with Patient-Reported Outcomes Following Cotton Osteotomy for Reconstruction of the Stage II Adult-Acquired Flatfoot Deformity; M. Conti, MD; First Published Jan. 18, 2019; Abstract Only.
A Comparision of Lateral Column Lengthening and Medial Translational Osteotomy of the Calcaneus for the Reconstruction of Adult Acquired Flatfoot, P. Bolt, et al; First Published Nov. 1, 2007; Abstract Only.
Treatment of Stage II Posterior Tibial Tendon Deficiency with Flexor Digitorum Longus Tendon Transfer and Calcaneal Osteotomy; Foot and Ankle International; M. Myerson MD, et al; First Published Jul. 1, 2004; Abstract Only.
Medial Displacement Calcaneal Osteotomy Using Minimally Invasive Technique; E. Kheir, et al.; Foot and Ankle International, first published Oct. 20, 2014; Abstract Only.
Effect of Calcaneal Lengthening on Relationships among the Hindfoot, Midfoot, and Forefoot; B. Sangeorzan, Foot & Ankle International; First Published Mar. 1, 1993; Abstract Only.
Approach and Treatment of the Adult acquired flatfoot deformity; E. Vulcano et al ; Published Jun. 2013; 19 pages.

* cited by examiner

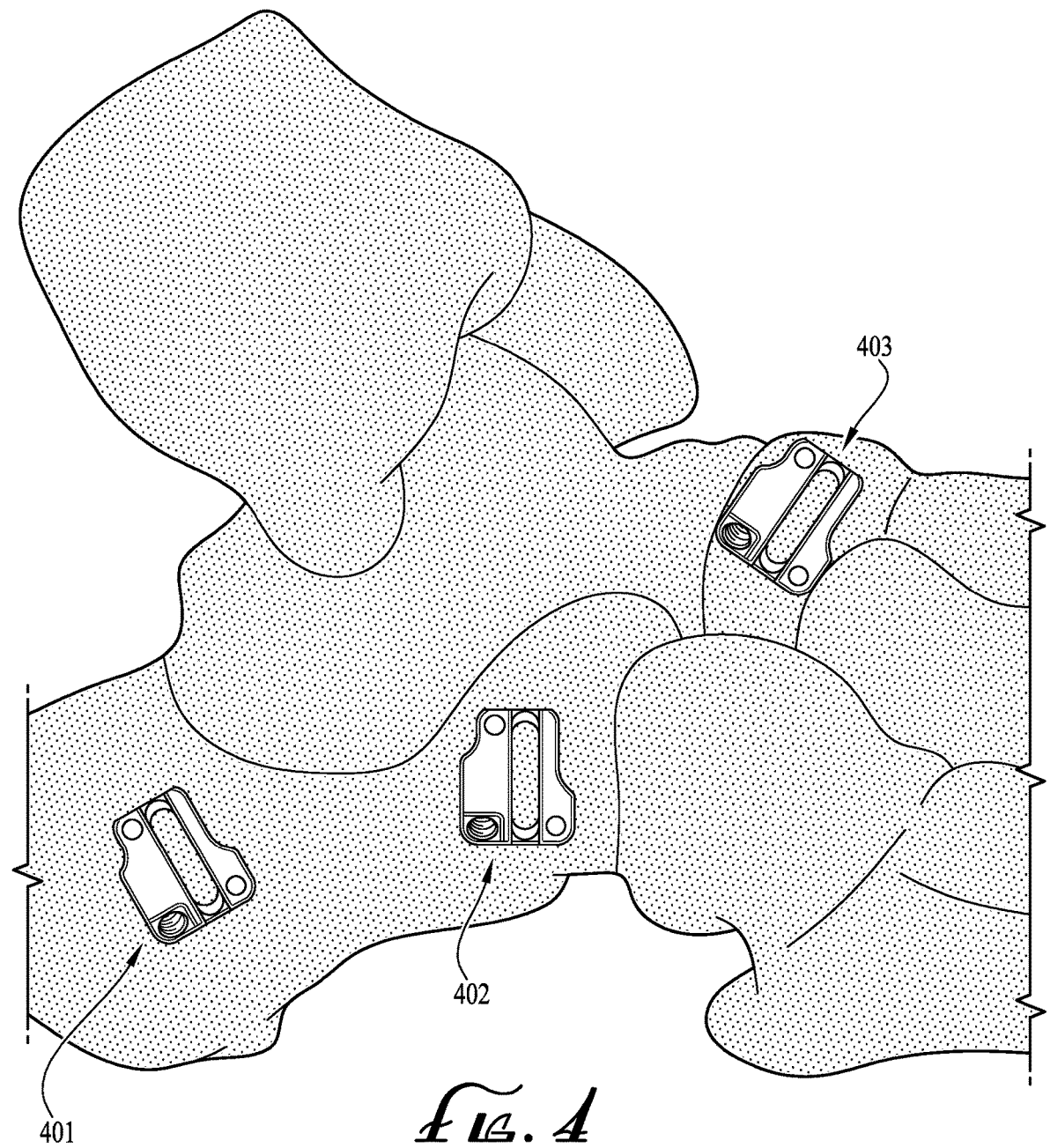

METHOD AND SYSTEM FOR MINIMALLY INVASIVE BONE EXTRA-ARTICULAR RECONSTRUCTION

CROSS-REFERENCE TO RELATED APPLICATION

This application claims the benefit of and priority from U.S. provisional application No. 62/867,850 filed on Jun. 27, 2019 and entitled Mini-Bone Extra-Articular Reconstruction (BEAR) System. The contents of the above application are hereby incorporated herein by reference in full.

FIELD OF INVENTION

This specification relates to a method and system for minimally invasive bone extra-articular reconstruction for pediatric or adult acquired flatfoot deformity.

BACKGROUND

The presently described invention provides an innovative method and system for performing corrective surgery for pediatric or adult acquired flatfoot deformity ("AAFD"), namely, minimally invasive bone extra-articular reconstruction ("BEAR"). The present invention provides a minimal incision, all bone, extra-articular reconstruction system that will replace the multiple long surgical incisions that accompany the traditional procedure with minimal ones. This type of surgery is technically difficult with a huge learning curve, the present invention dramatically reduces the difficulty. The present invention includes cutting guides that provide accurate straight cuts, make surgical procedure simpler and reproducible, reduce intra-operative X-ray exposure, reduce post-surgery recovery time, reduces operating room procedure time, produce better cosmetic results, and reduce narcotic use secondary to less pain by virtue of less surgical work on the patient.

Adult acquired flatfoot deformity is a complex, chronic debilitating condition characterized by a decrease in the medial arch height in which the talus is rotated in a medial and plantar position. The talonavicular coverage angle is decreased as the forefoot drifts into pronation and abduction. Often the Achilles tendon is shortened, exerting a valgus moment on the calcaneus and in combination with the above, leads to a pressure shift from the lateral column to the medial column with subsequent loss of the medial arch. In an adult, a diseased posterior tibial tendon ("PTT") is the usual culprit. Stage 2 disease after failure of conservative management would require surgery.

The operative treatment of stage 2 deformity has changed significantly over the last 40 years. Joint sparing procedures which aim to re-align the hindfoot and augment the diseased tibialis posterior tendon (flexor digitorum longus transfer, also known as FDL transfer), now have precedence over hindfoot fusions that are only typically used in stage 2 C disease or higher. The scientific evidence shows that the FDL transfer alone does not work. Moreover, the FDL transfer does not add substantial benefit because tendon strength studies show the relative strength of the posterior tibial tendon is 6.4 compared to the strength of the FDL which is 1.8, meaning that the FDL is only 28% the strength of the PTT. In addition, during the operative procedure, most surgeons have been taught to tighten the FDL transfer too tight, thus violating basic tendon strength biomechanical concepts.

Biomechanical tendon function work has shown that through the Blix curve (a diagram of tendon strength vs tendon length) the best tendon transfer strength is at resting length to 120% of length. Any tension above or below this leads to inherent weakness. This means that the typical FDL transfer is even weaker because of excess tension, its fragile strength in general, plus the fact that tendons lose some strength by virtue of the transfer process alone. The general believe is that corrective surgery involving calcaneal osteotomy is absolutely necessary to support the tendon transfer and soft tissue repair (the spring ligament). Biomechanical cadaver studies have shown that the addition of the spring ligament repair adds very little if anything to the maintenance of correction. In theory, the FDL transfer makes sense, it does not really do enough to warrant its long incision, increased surgery time and prolonged recovery. FDL transfer was introduced by Leonard Goldner in 1974 and popularized by Roger Mann in 1983. Current biomechanical evidence however questions its effectiveness. Research from University of Utah showed that the FDL transfer to the navicular reduced the capacity of the tendon to invert the hindfoot by 36% in comparison to leaving it at its resting state. Research from Lehigh University using multi-segmented foot modeling to assess the effectiveness of the medial displacement calcaneal osteotomy to correct the flatfoot showed no improvement in abnormal loading or deforming joint moments in the medial arch with the FDL transfer. Vaudreuil et. al. at in the Journal of Orthop Res. 2014 used a cadaveric robotic gait simulator to study the effects of the FDL transfer on a flatfoot model and found no improvement of foot alignment or function. Researchers at Virginia Commonwealth University studied cadaveric specimens and determined that the FDL transfer can actually increase loads on the medial arch and heel, exacerbating the deforming forces of the adult acquired flatfoot.

Thus, FDL transfer is unnecessary if the bone biomechanics of the foot are correctly restored with osteotomies. Based on this science, the present invention offers a minimal incision, all bone, extra-articular reconstruction ("BEAR") system that will do at least the following: (a) replace the multiple long surgical incisions that accompany the traditional procedure with minimal ones, (b) reduce post-operative recovery time by 40% (patients with the traditional transfer procedure are told 9-12 months recovery), (3) reduce operating room procedure time, (4) produce a better cosmetic result, and (5) reduce narcotic use secondary to less pain by virtue of less surgical work on the patient, which already has been substantially shown in minimally invasive osteotomy procedures elsewhere in the body.

Bone osteotomies in the treatment of the adult acquired flatfoot deformity include Medial Displacement Calcaneal Osteotomy (MDCO), Evans Procedure (lateral column lengthening), and Cotton Osteotomy (medial cuneiform osteotomy).

Regarding Medial Displacement Calcaneal Osteotomy (MDCO), Gleich in 1893 first described the calcaneal osteotomy in the treatment of pes planus. His original closing wedge osteotomy was performed in an oblique fashion through the posterior calcaneus with a dorsal apex restoring calcaneal inclination. In his technique, he cut the wedge wider medially to correct for pronation and displaced the heel medially and downward for correction of painful adult flatfeet. Although modified significantly over the years, the underlying principles essentially remain the same. That is, to restore the calcaneus to a neutral and biomechanically stable position.

Dwyer in 1959 reported using a posterior lateral calcaneal opening wedge osteotomy with placement of bone graft to correct severe valgus aligned feet. His thought was that the osteotomy restored the calcaneal weight-bearing axis, improved balance and changed the Achilles tendon force from an everting force to a neutral or inverting force.

The actual first MDCO in the treatment of AAFD (adult acquired flatfoot deformity) is credited to Koutsogiannis in 1971 with 34 patients. Since then, numerous authors including Mann, Myerson, Pomeroy and Manoli, Fayazi, Wacker, Guyton, Sammarco and Hockenbury have reported very favorable results after MCDO with tendon transfer (FDL (flexor digitorum languor) or FHL (flexor hallucis langus)) and spring ligament repair for the treatment of AAFD. MCDO is currently accepted as an established procedure for AAFD stage 2. MDCO has been reported to reduce contact stresses at the tibiotalar joint.

Cadaveric studies report increases in peak pressure over the lateral forefoot and heel. A translation of 10 mm substantially decreases first metatarsal load, medial arch load, and the moment at the talonavicular joint. MDCO also increases the load on the lateral foot, thus correcting the change in distribution of forces that happen with the failed tibialis posterior tendon ("PTT"). By allowing the Achilles tendon to effectively work better with the PTT, instead of against it, MDCO helps to supinate and stabilize the forefoot as a rigid lever arm during heel rise and propulsion. Brodsky noted significant improvements in the postoperative gait analysis for patients undergoing MCDO in conjunction with FDL transfer in terms of cadence, stride length and ankle push off. The role of the plantar fascia after osteotomy has been debated. The belief that it recreates the longitudinal arch by tightening the plantar fascia has been proven incorrect. It actually loosens the plantar fascia by 2.7 mm.

MDCO is predictable, reproducible, straightforward and reliable in terms of clinical results. Myerson reported 120 patients with MDCO, FDL transfer with spring ligament repair with great improvement in pain and function in 90%. However, radiographic arch improvement varies tremendously from patient to patient despite good clinical outcome. Moreover, radiographic improvements can be lost over time. Lastly, although there may be radiographic improvement in alignment and height of the medial longitudinal arch, the outer appearance may sometimes only be changed in a small number of patients.

The most common contraindications include rigid deformity and severe hindfoot degenerative arthritis. Complications are rare but most frequently are peroneal tendon irritation and/or sural neuritis. Nonunion is exceedingly rare because of a vast blood supply to the calcaneus. Screw head pain is common and may require removal after healing has occurred. Care must also be taken to avoid medial cortex penetration and damage to medial neurovascular structures. Sporadic cases of injury to medial structures have been reported. Posterior tibial arteriovenous fistula, tibial nerve palsy and lateral plantar nerve pseudoaneurysm have been noted.

Traditionally, the patient is placed in the supine position with a large roll under the ipsilateral hip. An incision of 5 to 7 cm in length is placed just inferior to the lateral malleolus at an approximate 45 degree angle to the weight bearing surface, avoiding the sural nerve and its branches as well as the peroneal tendons. Dissection straight down to bone is done with enough subsequent subperiosteal dissection to allow for the sagittal saw. Homan retractors are placed dorsally and plantarly around the bone to protect soft tissue structures. The osteotomy is then performed carefully, controlling the depth of the saw making sure to not over penetrate the medial cortex. An osteotome may often be used to complete portions of the medial cortex. A laminar spreader may be used to open the osteotomy and stretch the medial periosteum allowing for further displacement. With the foot held in plantar flexion to relax the intrinsic muscles, the osteotomy is held with provisional K-wires (Kirschner wires). The calcaneus is translated approximately 1 cm and then checked with axial images to assess the degree of displacement.

Fixation is usually performed with a large cannulated screw or side plate. Saxena et. al. in 2016 looked at 31 MCDO procedures; 17 fixed with a single screw and 14 with a locking side plate. 3 patients required plate removal as compared to one with the screw. No significant differences were noted with postoperative AOFAS scores ("American Orthopedic Foot And Ankle Score"). No mal-unions, non-unions, displacements or infections developed.

Malerba and DeMarchi have advocated the use of a Z osteotomy of the posterior tuberosity of the calcaneus. This combines a medial displacement of the calcaneal tuberosity and lateral column lengthening through an extensile (long incision) approach. The osteotomy allows the calcaneal tuberosity to be shifted medially or laterally. Removal of a laterally based wedge adds to the correction of heel varus in pes cavus surgery. The osteotomy incorporates a large bony surface and its inherent stability encourages early bone consolidation. It is held with staples or screws. Weight bearing is allowed at 6 weeks.

What is new and exciting is minimally invasive surgery ("MIS") in the foot because of its faster bone healing, quicker recovery, shorter operating room times and less pain. Recent advances in minimally invasive surgery have led to a number of advocates of this procedure for MDCO. Kendall and Ball in 2018 compared 50 open procedures to 32 MIS. A mean calcaneal displacement of 8 mm and 8.33 mm was achieved for the MIS group and open group respectively. There were significantly fewer wound complications in the MIS group (6.25%) compared to the open group (28%). MIS sural nerve complications were also significantly less. Jowett et. al. and Kheir and Borse also show 100% union rates with no wound or nerve complications in the later. Thus, MIS calcaneal osteotomy offers a safe alternative to open procedures with promising clinical results.

The present invention is a modification of MIS methods. Typically, in MIS MDCO, a small 4-5 mm incision is made and a burr is introduced. While it might work well in very experienced hands, there is a steep learning curve in MIS surgery. Difficulty for the surgeon is encountered with staying in the same plane with the burr (or wandering) which can lead to multiple unnecessary bone cuts affecting final alignment and healing. With the present invention, a K-wire will be introduced through a slightly larger incision (approximately 1 cm) at the site of the center of the cut, a cutting guide will be introduced over it (central wire is removed and guide then held by K-wires out of the plane of the cut) which will allow the surgeon to stay in the correct plane for 80-90% of the bone cuts, thus reducing surgeon error. Three cutting guides may be used, one providing a perpendicular cut to the bone, another providing a 10-15 degree distal to proximal cut and the latter cutting 10-15 degrees in a proximal to distal fashion.

The origins of lateral column lengthening procedure ("Evans procedure") come from a mistake made by a surgeon during the correction of a clubfoot. Although his original article was in 1959, Dilwyn Evans in 1961 published a series of relapsed clubfeet procedures. A portion of the surgery was to perform a calcaneocuboid shortening excision arthrodesis. In 2 failures, however, he noticed an overcorrection secondary to excessive bone excision, which caused a convex medial border and calcaneovalgus. Following attempted corrections with calcaneal osteotomies, he finally concluded that the shortened lateral column had produced lateral rotation of the navicular on the talus that could not be easily corrected by a mechanical shifting of the heel. Evans concluded that the lateral column had to be lengthened to medialize the heel, reduce the convexity of the medial border, reduced the navicular on the talus and restore the natural equinus of the foot. In Evan's 1975 article it is clear that he wanted to preserve the calcaneocuboid joint. He performed this procedure in 56 feet describing an osteotomy 1.5 cm proximal to the joint in a parallel fashion. The osteotomy was filled with ipsilateral tibial cortical bone and the patient was casted for 4 months. Mosca and others later modified the Evans procedure on the premise that the center of rotation for the correction is near the center of the talar head and not just the medial calcaneal cortex; therefore, the osteotomy is not a simple or plain distracting or opening wedge osteotomy. The direction of the osteotomy was modified by starting 1.5 cm proximal/lateral to the joint and headed distal/medial in an oblique fashion. They then recommended trapezoidal shaped tri-cortical iliac crest graft to fill the void.

The anatomic correction of the lateral column lengthening is probably the most powerful calcaneal osteotomy. Sangeorzan and associates compared pre-operative and post-operative radiographs and showed the lateral talocalcaneal angle improved 6.4 degrees, the talonavicular coverage improved 26 degrees and the calcaneal pitch by 10.8 degrees. DuMontier, in a cadaver flatfoot model, further verified the positional effects of the Evans procedure. The structure of the talar head affects the movement of the navicular around it. The head is wider in a medial-lateral direction than a dorsal-plantar one. As the lateral column is lengthened, there is medial movement of the forefoot at the transverse tarsal joint. In addition, the navicular moves slightly plantar resulting in forefoot adduction and plantarflexion with increased arch height. The navicular rotated 18.6 degrees of adduction, 2.6 degrees of pronation, 3.4 degrees of plantarflexion. 5.6 mm medial, 0.4 mm posterior and 1.8 mm plantar. The cuboid rotated 24.2 degrees of adduction, 13.9 degrees of pronation, 1.9 degrees of plantarflextion, 9.4 mm medial, 2.6 mm distal, and 1.5 mm plantar. The calcaneus did not move into varus relative to the talus or tibia, suggesting that the it is the midfoot and forefoot correction that gives the appearance of calcaneovarus.

The Evans osteotomy has a 3 dimensional effect that renders it an essential component in the surgical management of the flexible valgus flatfoot. Complications are of low incidence and are related to patient selection, surgical approach and foot geometry correction. Non-union is infrequent and varies from 1.4%-5.26%. Dorsal subluxation of the anterior tuberosity of the calcaneus can frequently occur but often self corrects.

Lateral column overload can occur if the magnitude of the correction is too great. Calcaneal cuboid arthritis is of very low incidence and is not always attributable to the osteotomy. Although intra-articular joint pressures increase after osteotomy, there is no biomechanical study that indicates an intra-articular pressure threshold associated with calcaneocuboid joint arthritis. In almost all publications, the size of the graph fluctuates between 6 and 12 mm. Cadaveric studies however, show that pressure in the calcaneocuboid joint begins to increase when the graft is greater than 8 mm and increases significantly with respect to a normal foot with grafts greater than 10 mm wide. It is recommended that if greater correction is necessary, combine the osteotomy with other complimentary procedures. Sural nerve injury has been reported at an incidence of 11% by Thomas. The peroneus longus tendon is at risk if the osteotomy is done less than 10 mm from the joint. The subtalar joint middle facet is at risk with osteotomy performed at 1.5 cm proximal to the joint. Hyer et. al. showed in a cadaver study that 56% of calcanei have a conjoined anterior and medial facet, 3% had an absent anterior facet and 41% had separate facets. They also found that the mean distance between the anterior border of the calcaneus to the proximal edge of the anterior facet was 11.04 mm and the mean separation between the anterior and middle facets when present was 3.85 mm. They therefore concluded that ideal starting point for the Evans osteotomy is between 11 and 15 mm from the calcaneocuboid joint.

Bussewitz later showed that starting 1.3 cm proximally and angling obliquely distally (like Mosca), reduced injury to the sustentaculum tali and medial facet. Over-correction is rare and associated mainly with spastic flatfeet. Under-correction is also rare and mostly seen in cases of talocalcaneal coalitions. Achilles tendon lengthening is also important in the avoidance of under-correction and recurrence. Current literature supports the Evans over calcaneocuboid joint fusion because of higher complication rates in fusion patients.

Regarding Evans osteotomy, the patient is positioned in the lateral position with a hip roll to internally rotate the leg. An incision is made 5-7 cm in length, starting at the calcaneocuboid joint and extending proximally in line with the superior border of the calcaneus. Care is taken to avoid and protect the sural nerve and peroneal tendons plantarly and the intermediate dorsal cutaneous nerve dorsally. The joint capsule is not violated. A retractor is introduced to protect soft tissues and give exposure. Subperiosteal dissection is done enough to allow usage of a saw or osteotome. At 1.1 cm to 1.3 cm proximal to the joint the osteotomy is done, either straight transverse or slightly distal oblique. A laminar spreader is introduced to open the osteotomy and it is filled with a bone graft wedge, autograph or allograft depending on the surgeon preference. Fixation with a plate, screw or staple is done. Some surgeons do not fixate at all claiming that the compression provided by the osteotomy is enough. The patient is casted or placed in a walking boot, non-weight bearing for 6 weeks, then progressed according to radiographic follow up.

A Z-lengthening osteotomy has been advocated by Griend and also by Scott and Berlet. This procedure uses a distal vertical cut 10 mm proximal to the calcaneocuboid joint through the dorsal half of the anterior process which is connected to a horizontal limb, full thickness through the calcaneus and finally completed by a vertical plantar cut at the level of the peroneal tubercle. Although patient numbers are small, results are good. It is technically more demanding and should be considered as an additional option for surgeons.

The present invention is the first to introduce the concept of MIS to the Evans procedure. A one centimeter incision obliquely along the natural skin lines of the lateral foot with the center being 1-1.5 cm proximal to the calcaneocuboid joint is made. Subperiosteal dissection is done superiorly and inferiorly and the cutting guide is introduced over a K-wire placed in the center of the future cut, 1.3 mm from the calcaneocuboid joint. For surgeons that want to do a perpendicular cut, a straight cut guide will exist. Based on the literature and the need for a slightly oblique cut, a cutting guide with a 10-15 degrees angle from proximal lateral to medial distal is used to protect the medial facet of the subtalar joint. A smooth laminar spreader or a distraction device may be used with the K-wires that have been holding the cutting guide to distract the osteotomy. Because of the 2 mm bone loss from the burr, a 10 mm wedge may be introduced (producing 8 mm of correction). To ensure maintenance of the displacement (no collapse of graft), a titanium wedge or cage is recommended. However, as previous described, cortical bone wedge can be used effectively. To effectively measure the desired amount of graft for correction, a triangular wedge shaped 'Popsicle" is introduced. Sizes may vary from 6 to 10 mm. This will help pick the graft size. Once this is done, the actual graft is inserted. No fixation is necessary, but that is the surgeon's preference.

Double calcaneal osteotomy includes a MDCO with a lateral column lengthening. First introduced by Frankel in 1995, the MCDO corrects the hindfoot valgus and the lateral column lengthening corrects the forefoot abduction and increases arch height. Sharing the correction reduces the pressures on each osteotomy individually resulting in a more anatomic correction of the deformity and lessening of recurrence. Done the traditional way, there are two large incisions within close proximity of each other lending to wound complications. The present invention provides the combination of MIS MDCO and Evans to achieve the same result with small incisions and reduce wound complications.

A plantar flexion opening wedge medial cuneiform osteotomy ("Cotton osteotomy") was first described by Cotton in 1936 in order to restore a plantigrade foot has stood the test of time to treat residual supination of the midfoot after correction of the hindfoot valgus deformity in reconstruction of the stage 2 AAFD.

Supination of the medial longitudinal arch is thought to be a secondary deformity that occurs as a compensatory mechanism in order to maintain a plantigrade foot in the setting of persistant hindfoot valgus. Subsequent studies have demonstrated that the Cotton osteotomy has a high rate of union, maintains mobility of the first ray and allows the surgeon to titrate the amount of necessary correction.

The Cotton osteotomy is most often done with other procedures. Meary's angle (the long axis lateral talar-first metatarsal angle) has been used to evaluate flatfoot on the medial column with zero being normal. With this angle, the long axis of the talus is angled plantarly in pes planus. Castaneda et. al. developed a new radiographic measurement—the cuneiform articular angle (CAA) which is defined as the angle between the proximal and distal articular surfaces of the medial cuneiform on lateral weightbearing radiographs. The average change over 6.5 months was 6.5 degrees in their study. Kunas et. al. has shown that the size of the graft determines the associated changes in the CAA. Each millimeter of graft size corresponded to an approximate 2.1 degrees of change. Conti et. al. looked at 63 patients that had undergone Cotton procedures and concluded that excessive plantarflexion yields negative results. These patients experienced sesamoid pain, first metatarsal pain and also discomfort in the midfoot. Additional studies have also shown that over-correction in the plantarflexion and adduction planes can yield poor results.

The Cotton osteotomy tends to do more to the plantarflexion of the first metatarsal than it does to the medial arch signifying the importance of the medial longitudinal arch correction done by other methods. It must be remembered that if there is medial column instability or degenerative arthritis, then a fusion at the isolated unstable or arthritic joint is the correct procedure, not the Cotton.

Complications include sesamoid pain from over-correction, under-correction, saphenous nerve or vein injury, graft displacement, tendon injury and proximal joint pain. Delayed union can be seen, but non-union is rare. In 2011, Lutz and Myerson evaluated 81 Cotton procedures. They reported 10 complications: 3 painful screws, 2 painful medial cuneiform exostosis, 1 plantar fasciitis, 1 painful sesamoid, 25th metatarsal overloads and 1 recurrence in a patient that later had a MDCO performed to eradicate pain. The others resolved with screw removal, orthotics or medial cuneiform exostectomy.

In AAFD, other procedures will have been performed before the Cotton. These usually include an Achilles lengthening, Evans procedure and possible MDCO. The present invention is the first to introduce MIS to the Cotton procedure. In the traditional way, with the patient in the supine position, a 3-4 cm dorsal longitudinal incision is made over the medial cuneiform. Care is taken to avoid the medial cutaneous nerve and saphenous vein and nerve medially and the extensor hallucis longus tendon laterally. Subperiosteal dissection is done to expose bone making sure to not disrupt adjacent ligaments and the anterior tibial tendon plantar medially. Under fluoroscopy the first metatarsal cuneiform and navicular cuneiform joints are identified. In the middle of the cuneiform a transverse cut is made leaving the plantar cortex intact. A smooth laminar spreader or a distractor device is used to open the osteotomy. A bone graft wedge is introduced varying in size from 4-6 mm. Fixation is usually not necessary.

The technique the present invention for Cotton osteotomy includes an approximate 1 cm dorsal longitudinal incision. Subperiosteal dissection is done minimally and a K-wire is placed near the center of the bone just proximal to the second metatarsal cuneiform joint and parallel to the first metatarsal cuneiform joint. Dissection as needed is done to place the cutting guide centrally over the K-wire. It is then fixed with adjacent wires and the central wire removed. A burr is then used to cut bone being aware of surrounding structures. A narrow osteotome may be used to complete cuts. The joint is distracted with a smooth laminar spreader or distraction device and the "Popsicle" trial triangular graft is introduced for sizing. Once the appropriate size is discovered, the actual graft is inserted. To avoid over-correction, a 4-6 mm cortical bone wedge or titanium cage is recommended. Again, fixation is not necessary.

Calcaneal osteotomies have been shown to be extremely powerful procedures in the correction of AAFD. Soft tissue corrections alone are doomed to fail. Because of the inherent weakness of the FDL transfer and its need for significant osteotomies to provide a plantigrade foot for its survival, the FDL transfer is not necessary. The present invention includes an all bone, minimally invasive technique with instrumentation that will get the same magnitude of bony correction as an open procedure and will also yield similar if not better post-operative results. Patients will experience a quicker recovery, less pain, less operating room time, less narcotic use, and a better cosmetic result from smaller incisions.

SUMMARY

It is an objective of this invention to provide a method and system for replacing the multiple long surgical incisions that accompany the traditional procedure with minimal incisions.

It is a further objective of this invention to provide a cutting guide to reduce surgeon error.

It is a further objective of this invention to reduce post-surgery recovery time.

It is a further objective of this invention to reduce operating room procedure time.

It is a further objective of this invention to produce a better cosmetic result

It is a further objective of this invention to reduce narcotic use by virtue of less surgical work on the patient.

It is a further objective of this invention to make surgery simpler and reproducible.

It is a further objective of this invention to reduce intra-operative X-ray exposure.

These and other objectives are preferably accomplished by providing a method and system comprising attaching a cutting guide to the bone to be operated wherein the cutting guide comprises two or more diverging K-wire channels and a slit configured to guide a burr used by a surgeon to perform osteotomy through the slit. Through the use of the cutting guide, the surgical procedure is simpler and reproducible. Patients will experience a quicker recovery, less pain, less operating room time, less narcotic use, and a better cosmetic result from smaller incisions. The present invention may also be applicable to intra-articular applications.

These and other aspects of this invention will become apparent to those skilled in the art after reviewing the following description of the invention.

BRIEF DESCRIPTION OF THE DRAWINGS

FIG. 4 is an illustration of an embodiment of applying cutting guides of the present invention to a foot ankle;

DETAILED DESCRIPTION AND PREFERRED EMBODIMENT

The detailed description of exemplary embodiments herein makes reference to the accompanying drawings and figures, which show the exemplary embodiments by way of illustration and best mode. While these exemplary embodiments are described in sufficient detail to enable those skilled in the art to practice the invention, it should be understood that other embodiments may be realized and that logical changes may be made without departing from the spirit and scope of the invention. Thus, the detailed description herein is presented for purposes of illustration only and not of limitation. Moreover, any reference to singular includes plural embodiments, and any reference to more than one component may include a singular embodiment.

Figure 1A:
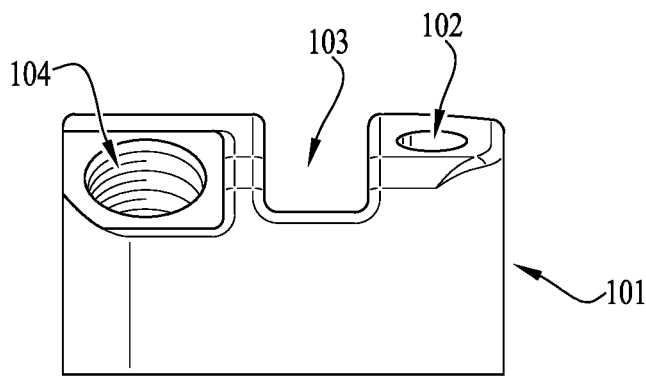
FIG. 1A is a front view of an embodiment of the cutting guide of the present invention.
Figure 1B:
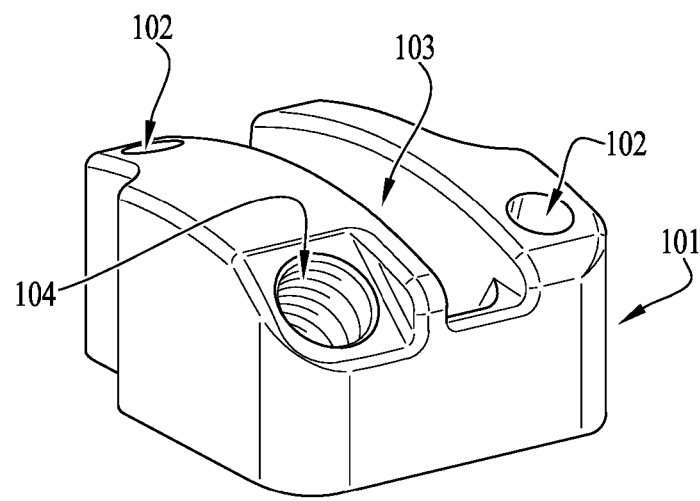
FIG. 1B is a perspective view of the embodiment as described in FIG. 1A.
Figure 1C:
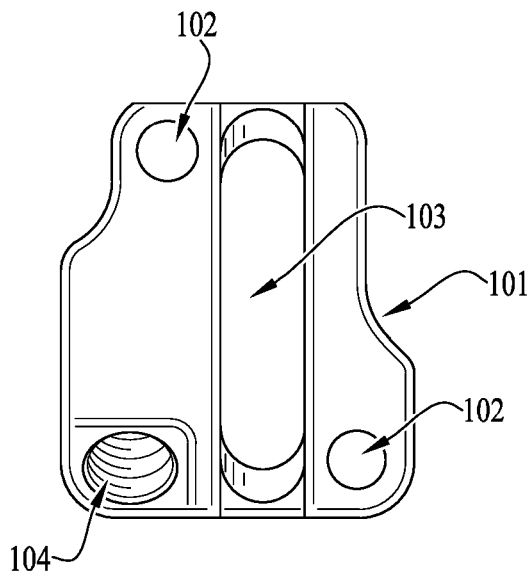
FIG. 1C is a bottom view of the embodiment as described in FIG. 1A.
Figure 2:
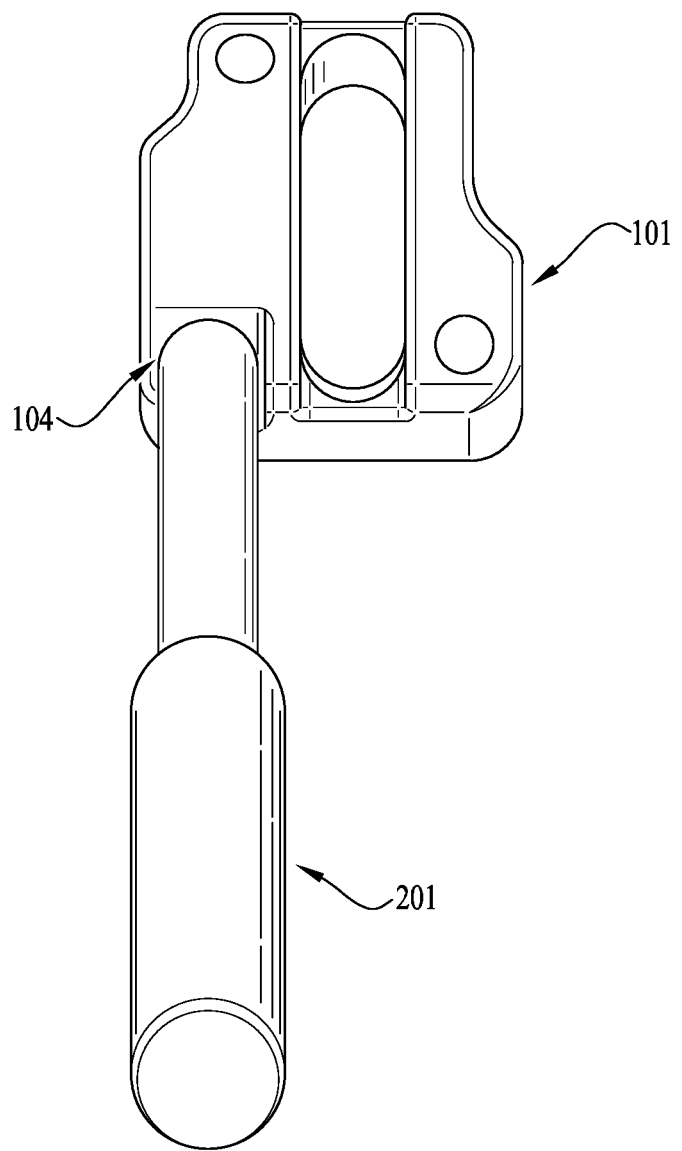
FIG. 2 is a perspective view of an embodiment of the cutting guide of the present invention.
Figure 3A:
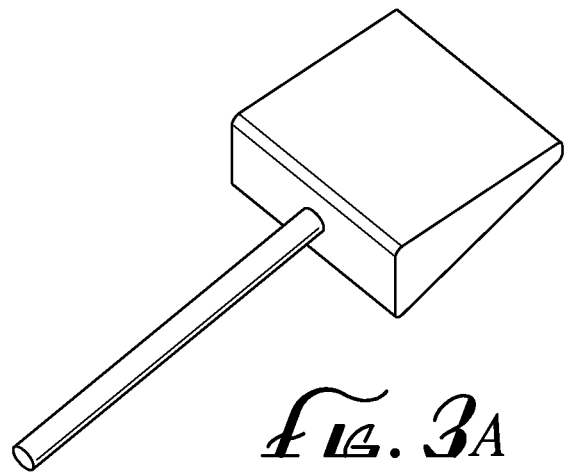
FIG. 3A is a perspective view of an embodiment of popsicle.
Figure 3B:
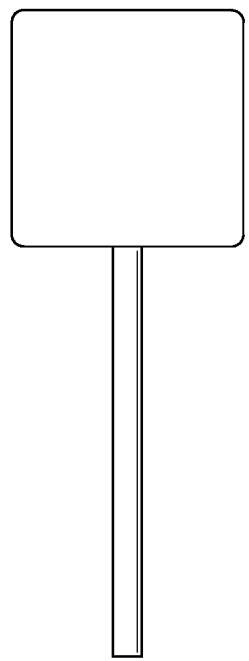
FIG. 3B is a side view of the embodiment described in FIG. 3A.
Figure 3C:
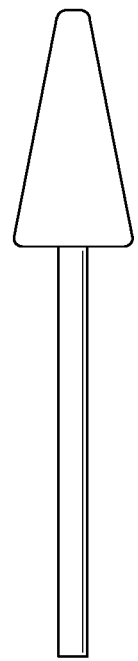
FIG. 3C is a another side view of the embodiment described in FIG. 3A.
Figure 3D:
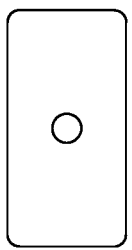
FIG. 3D is a bottom view of the embodiment described in FIG. 3A.

FIGS. 1A and 1B disclose a front view and perspective view of an embodiment of the cutting guide of the present invention. FIG. 1C discloses a top view of the embodiment. The cutting guide includes a rigid body 101, two channels 102 that travel through the rigid body 101, a longitudinal slit 103 that provides guidance to a burr for performing osteotomy, and a threaded hole 104 for attaching a handle. FIG. 2 illustrates a handle 201 attached to the rigid body 101 through the threaded hold 104. In addition to treading, the hole 104 may use other mechanism, such as grooving or snapping, for attaching a handle. Instead of in a direction perpendicular to the bottom surface of the cutting guide, the channels 102 are tilted relative to the bottom surface of the cutting guide so that the cutting guide is more secured when k-wires are attached to a bone through the channels.

Figure 1D:
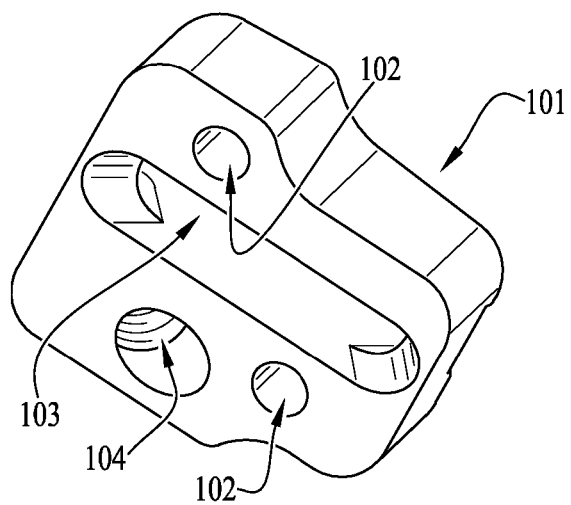
FIG. 1D is a bottom perspective view of the embodiment as described in FIG. 1A.

FIG. 1D provides a bottom view of the cutting guide. As shown, the threaded hole 104 also goes through the rigid body 101; however, it may not need to. K-wires are inserted through the channels 102 and attach to the bone to be operated on so that the cutting guide's bottom is secured thereon. A burr is inserted through the slit 103 while performing osteotomy so that the movement of the burr is guided by the slit 103.

Traditionally, extra-articular bone osteotomies are done through open procedures that requires a relatively larger incision (usually 4 to 5 centimeters), where surgeons rely on their experienced hand to perform osteotomies with burrs of different sizes. This leads to inconsistency. By using the cutting guide which is relatively small, approximately 1 to 1.5 centimeters in length, only a small incision, approximately 1 centimeter, is needed to insert the cutting guide and attach it onto the bone to be operated. The size of the cutting guide may vary depending on the need. To perform osteotomy, the burr is inserted through the slit of the cutting guide, which guides the movement of the burr and provides consistency. In other embodiments (not shown), the instead of in a straight longitudinal direction, the slit of the cutting guide may of other shape, for example V shape, in order to accommodate the need of osteotomies.

FIGS. 3A through 3D illustrate different views of an embodiment of a triangular wedge popsicle (3A: a perspective view, 3B and 3C: side views, 3D: bottom view). A popsicle is used to effectively measure the amount of bone graft needed or desired. The popsicle's size varies from 6 to 10 mm. Once the amount of bone graft is determined, the popsicle is removed and the actual graft is inserted.

Figure 5A:
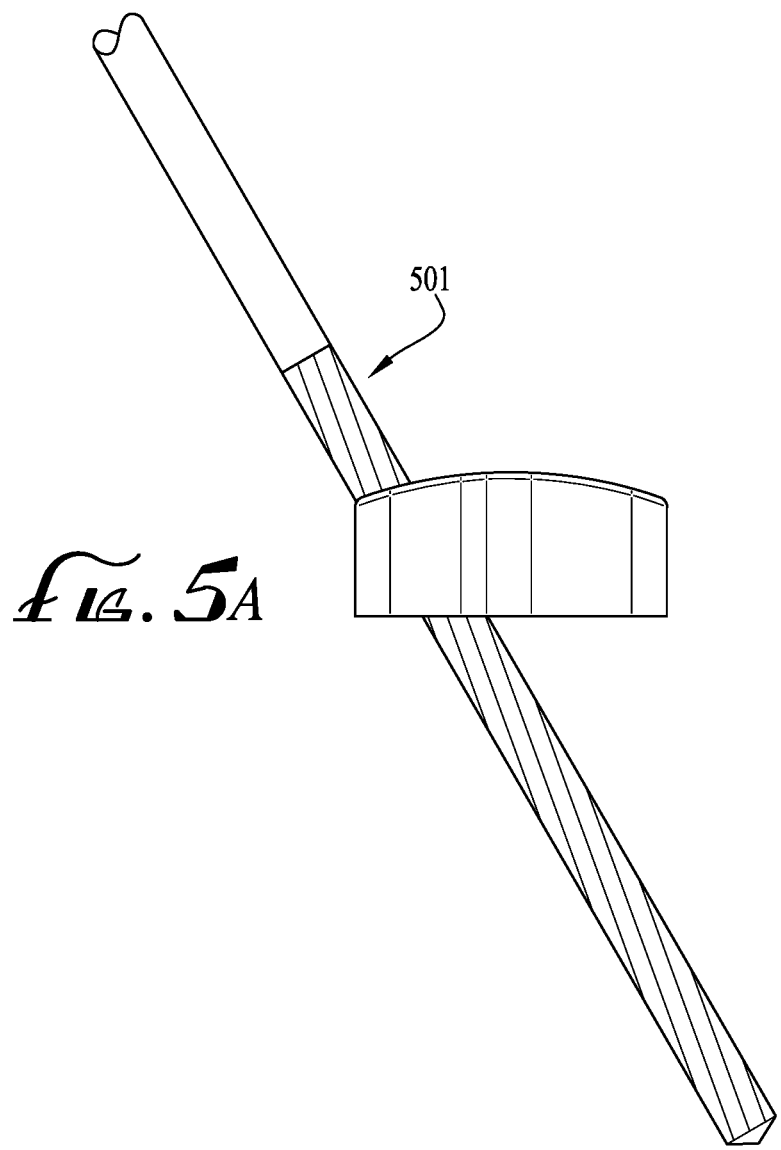
FIG. 5A is a side view of a burr traveling through an embodiment of the cutting guide of the present invention.
Figure 5B:
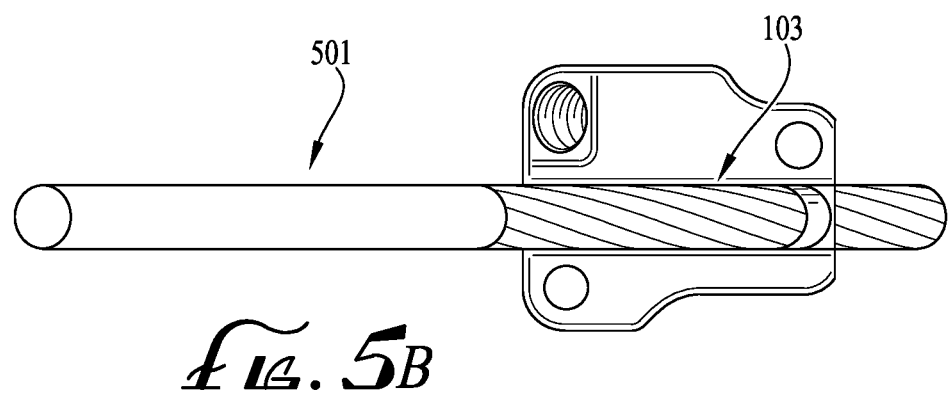
FIG. 5B is a side view of the embodiment as described in FIG. 5A.
Figure 5C:
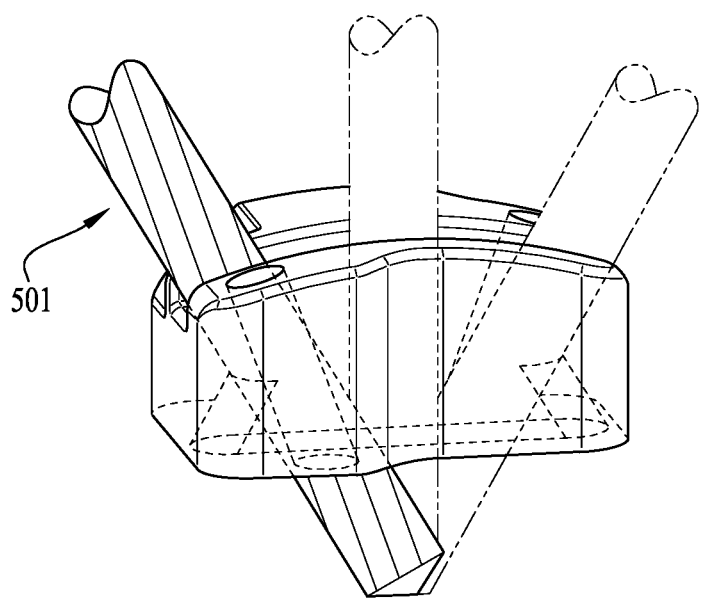
FIG. 5C is an illustration of different angles of the burr traveling through an embodiment of the cutting guide of the present invention.
Figure 5D:
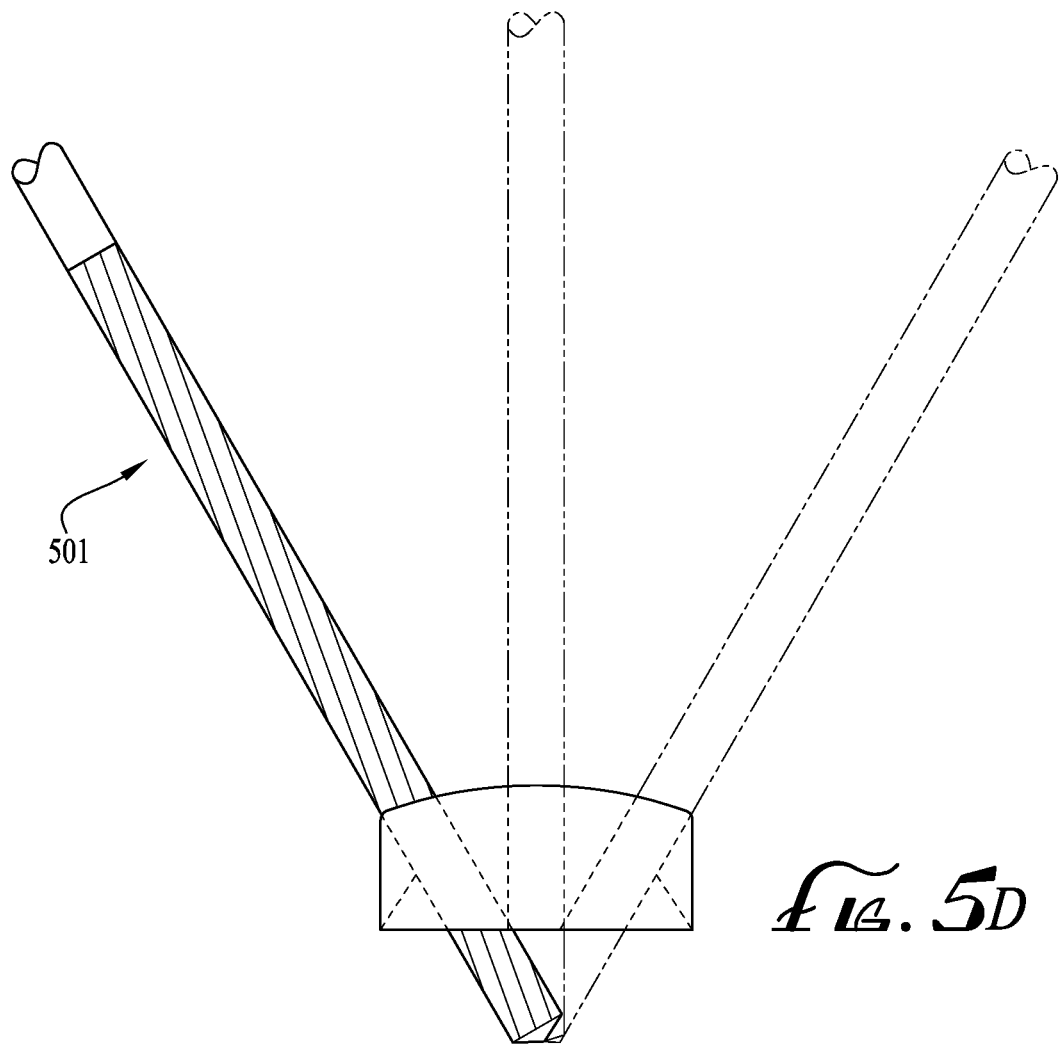
FIG. 5D is another illustration of the embodiment as described in FIG. 5C.

Referring to FIGS. 5A and 5B, a burr 501 inserted through an embodiment of the cutting guide is disclosed. As shown, the burr 501 is snuggly fit within the slit 103. The burr is guided so that it may only move longitudinally instead of laterally. The width of the slit ranges from 2 mm to 3 mm depending on the size of the burr. The burr may move in various angles along the plane parallel to the slit as needed. See, FIGS. 5C and 5D. Furthermore, once osteotomy on one bone location is finished, the cutting guide may be move to another location or orientation for further osteotomy as needed.

FIG. 4 illustrates the various osteotomy procedures for pediatric or adult acquired flatfoot deformity where the cutting guide of the present invention may be used, including MCDO procedure 401, Evans procedure 402, and Cotton procedure 403. Additional foot/joint procedures include MTP fusions, Subtalar fusions, Midfoot fusions, Ankle fusions, Lapidus procedure, and Triple arthrodesis. Other extra-articular bone osteotomies may be in the tibial with supramalleolar osteotomies, proximal tibial osteotomies and fibula osteotomies. Zadek calcaneal osteotomy and Malerba osteotomies may also be performed using the cutting guides. The cutting guide may also be used in procedures for upper extremities. The present invention will have broader use in the bones in the foot and ankle, including metatarsal, phalanges, cuneiform, cuboid, navicular and talus bones.

In practice, for foot correction surgery, the Achilles/gastrocnemius lengthening is performed first. The lateral column lengthening is next with insert of popsicle with measurement. Then the heel is examined to see if this added enough varus correction. If the answer is yes, the Cotton procedure or medial column stabilization is performed. If not, then the MDCO procedure is performed. Then go to the medial column and add Cotton osteotomy with popsicle and measure. Now the entire correction can be examined. If the result is approved, final bone graft wedges or titanium wedges are then added.

The previous description of the disclosed examples is provided to enable any person of ordinary skill in the art to make or use the disclosed method and apparatus. Various modifications to these examples will be readily apparent to those skilled in the art, and the principles defined herein may be applied to other examples without departing from the spirit or scope of the disclosed apparatus. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope. Skilled artisans may implement the described functionality in varying ways for each particular application, but such implementation decisions should not be interpreted as causing a departure from the scope of the disclosed apparatus.

What is claimed is:

1. A cutting guide for osteotomy to correct pediatric or adult flatfoot deformity comprising:
    a rigid body comprising a top surface, a bottom surface, two or more channels, and a longitudinal slit wherein:
    the bottom surface is adapted to be in contact with a bone;
    the longitudinal slit comprises an access allowing a burr to travel through the rigid body to be in contact with the bone, the width of longitudinal slit is configured to allow the burr to move along the longitudinal slit longitudinally without substantial lateral movement;
    each of the two or more channels comprises a proximal open end at the top surface and a distal open end at the bottom surface, each of the two or more channels is configured to provide access for one or more k-wires to travel through the rigid body from the proximal open end to the distal open end;
    the proximal open end of one of the two or more channels is not vertically aligned with the distal open end of the one of the two or more channels so that the one of the two or more channels is at an angle relative to the bottom surface, that is, not perpendicular to the bottom surface so that the burr has a greater arc of motion in the longitudinal slit.

2. The cutting guide of claim 1, wherein the rigid body further comprising a hole configured to be attached a handle.

3. The cutting guide of claim 1, wherein the length of the longitudinal slit ranges between 1 to 1.5 centimeters.

4. The cutting guide of claim 1, wherein the width of the longitudinal slit ranges between 2 to 3 millimeters.

5. The cutting guide of claim 2, wherein the hole travels through the rigid body from the top surface to the bottom surface.

6. A method for performing minimally invasive bone extra-articular reconstruction comprising the following steps:
    (1) locating a site for making a small incision proximal to a bone for osteotomy;
    (2) making the small incision of approximately 1 centimeter in length at the site;
    (3) inserting a cutting guide through the small incision wherein the cutting guide comprises a rigid body comprising a top surface, a bottom surface, two or more channels, and a longitudinal slit wherein:
    the bottom surface is adapted to be in contact with the bone;
    the longitudinal slit comprises an access allowing a burr to travel through the rigid body to be in contact with the bone, the width of longitudinal slit is configured to allow the burr to move along the longitudinal slit longitudinally without substantial lateral movement;
    each of the two or more channels comprises a proximal open end at the top surface and a distal open end at the bottom surface, each of the two or more channels is configured to provide access for one or more k-wires to travel through the rigid body from the proximal open end to the distal open end;
    the proximal open end of one of the two or more channels is not vertically aligned with the distal open end of the one of the two or more channels so that the one of the two or more channels is at an angle relative to the bottom surface, that is, not perpendicular to the bottom surface so that the burr has a greater arc of motion in the longitudinal slit;
    (4) inserting one or more k-wires through the two or more channels in order to attach the cutting guide to the bone for osteotomy;
    (5) inserting a burr through the small incision and the longitudinal slit of the cutting guide in order to perform osteotomy on the bone;
    (6) using the longitudinal slit of the cutting guide to guide the movement of the burr and thereby reducing the need of intra-operative X-ray during osteotomy surgery.

7. The cutting guide of claim 6, wherein the rigid body further comprises a hole configured to be attached a handle.

8. The cutting guide of claim 6, wherein the length of the longitudinal slit ranges between 1 to 1.5 centimeters.

9. The cutting guide of claim 6, wherein the width of the longitudinal slit ranges between 2 to 3 millimeters.

10. The cutting guide of claim 7, wherein the hole travels through the rigid body from the top surface to the bottom surface.

\* \* \* \* \*